United States Patent [19]

Anazawa et al.

[11] Patent Number: 5,217,883
[45] Date of Patent: Jun. 8, 1993

[54] PROCESS FOR PRODUCING AMINO ACID

[75] Inventors: Hideharu Anazawa, Tokyo; Hiroaki Motoyama, Yokohama; Sadao Teshiba, Machida, all of Japan

[73] Assignee: Kyowa Hakko Kogyo Co., Ltd., Tokyo, Japan

[21] Appl. No.: 739,426

[22] Filed: Aug. 2, 1991

[30] Foreign Application Priority Data

Aug. 2, 1990 [JP] Japan .................................. 2-205567

[51] Int. Cl.$^5$ ..................... C12R 1/01; C12R 13/04; C12R 13/08
[52] U.S. Cl. .................................. 435/115; 435/106; 435/252.3; 435/252.31; 435/822; 435/172.1
[58] Field of Search ..................... 435/106, 822, 172.1, 435/252.3, 252.31, 115

[56] References Cited

U.S. PATENT DOCUMENTS 3,907,637  9/1975  Nakayama et al. .
3,907,641  9/1975  Nakayama et al. .

FOREIGN PATENT DOCUMENTS 49-125590 12/1974 Japan .
50-25790   3/1975 Japan .
52-18886   2/1977 Japan .
1-235595   9/1989 Japan .

OTHER PUBLICATIONS

Japanese Patent Abstract No. 70-25273 "Production of Amino Acids by Fermentation".
APS JP0ABS Araki et al. Japan 01-235595 (Sep. 20, 1989).

*Primary Examiner*—Herbert J. Lilling
*Attorney, Agent, or Firm*—Antonelli, Terry, Stout & Kraus

[57] ABSTRACT

Disclosed is a process for producing amino acids such as L-threohine and L-lysine, which comprises culturing, in a medium containing methanol as a major carbon source, a microorganism which belongs to the genus Methylobacillus and which has an ability to produce the amino acid(s) and resistance to at least one member selected from the group consisting of L-threonine, L-lysine and an amino acid analogue, said microorganism being obtained by mutation of a parent strain which belongs to the genus Methylobacillus and which has an enhanced sensitivity to at least one of an antibiotic and an amino acid analogue; allowing the amino acid(s) to accumulate in the culture; and recovering the amino acid(s) therefrom.

6 Claims, No Drawings

PROCESS FOR PRODUCING AMINO ACID

BACKGROUND OF THE INVENTION

The present invention relates to a process for producing amino acids such as L-threonine and L-lysine by fermentation. The amino acids are widely utilized in the fields of drugs, foodstuff, animal feed, etc.

Heretofore, with regard to production of amino acids from methanol which is a starting material for fermentation available in large quantities at low cost, there are known processes in which microorganisms belonging to various genera are used; for example, microorganisms of the genus Achromobacter and the genus Pseudomonas (Japanese Published Examined Patent Application No. 25273/70), the genus Protaminobacter (Japanese Published Unexamined Patent Application No. 125590/74), the genus Protaminobacter and the genus Methanomonas (Japanese Published Unexamined Patent Application No. 25790/75), and the genus Microcyclus (Japanese Published Unexamined Patent Application No. 18886/77). However, the amounts of amino acids produced are small and are not satisfactory in these known processes.

SUMMARY OF THE INVENTION

According to the present invention, amino acids such as L-threonine and L-lysine can be produced in high yields and at low cost by culturing, in a medium containing methanol as a major carbon source, a microorganism which belongs to the genus Methylobacillus and which has an ability to produce the amino acid(s) and resistance to at least one member selected from the group consisting of L-threonine, L-lysine and an amino acid analogue, said microorganism being obtained by mutation of a parent strain which belongs to the genus Methylobacillus and which has an enhanced sensitivity to at least one of an antibiotic and an amino acid analogue; allowing the amino acid(s) to accumulate in the culture; and recovering the amino acid(s) therefrom.

DETAILED DESCRIPTION OF THE INVENTION

Any microorganism can be used in the present invention, so long as it has the following properties: (1) it belongs to the genus Methylobacillus; (2) it is obtained by mutation of a parent strain belonging to the genus Methylobacillus which has an enhanced sensitivity to at least one of an antibiotic and an amino acid analogue; (3) it has resistance to at least one member selected from the group consisting of L-threonine (hereinafter abbreviated as L-Thr), L-lysine (hereinafter abbreviated as L-Lys) and an amino acid analogue; (4) it can grow in a medium containing methanol as a major carbon source; and (5) it has the ability to produce amino acids, especially L-Thr or L-Lys. A mutant having such properties can be obtained by subjecting the parent strain to a conventional mutational treatment such as ultraviolet irradiation, a treatment with N-methyl-N'-nitro-N-nitrosoguanidine (NTG), or the like.

Examples of the antibiotic are kanamycin, ampicillin and streptomycin.

Examples of the amino acid analogue are α-amino-β-hydroxyvaleric acid (hereinafter abbreviated as AHV), S-2-aminoethyl-L-cysteine (hereinafter abbreviated as AEC) and DL-4,5-transdehydrolysine (hereinafter abbreviatedas DHL).

Specific examples of the microorganism used in the present invention are shown in Table 1.

TABLE 1

| Strain | Resistance |
| --- | --- |
| Methylobacillus sp. TA-47 | L-Thr |
| Methylobacillus sp. DA-19 | L-Lys + AHV |
| Methylobacillus sp. DA-35 | DHL |
| Methylobacillus sp. AL-76 | L-Lys + AHV |
| Methylobacillus sp. TR-26 | L-Thr |
| Methylobacillus sp. ATR-89 | L-Thr + AEC |

The procedures for obtaining these strains are shown below.

Wild strains of bacteria belonging to the genus Methylobacillus have a low sensitivity to an amino acid analogue, so that it is difficult to confer resistance to the amino acid analogue on the wild strains and isolate mutants which are released from metabolic regulation. The reason why these strains have a low sensitivity to the amino acid analogue is believed to be their poor membrane permeability to various chemicals. Therefore, amino acid leaky mutants are induced from the wild strains, and a strain which shows an enhanced sensitivity to various chemicals and an improved permeability to the chemicals is selected as a parent strain from the thus obtained mutants.

As the parent strain, there may be used a strain belonging to the genus Methylobacillus and having an enhanced sensitivity to at least one member selected from antibiotics such as kanamycin, ampicillin and streptomycin and amino acid analogues such as AHV and AEC. For example, in addition to already known strains, there may be used mutants of wild strains such as *Achromobater methanolophila* ATCC 21452, *Pseudomonas insueta* ATCC 21276, *Protaminobacter thiaminophagus* ATCC 21371 and *Methanomonas methylovora* ATCC 21369 which have an enhanced sensitivity to the chemicals mentioned above. Examples of the already known strains are *Pseudomonas insueta* K-015 (ATCC 21966), *Pseudomonas insueta* K-038 (ATCC 21967) and *Protaminobacter thiaminophagus* K-224 (ATCC 21969).

It is described in International J. Systematic Bacteriology, 27, 247-255, 1977, ibid., 34, 188-201, 1984 that ATCC 21452 strain, ATCC 21276 strain, ATCC 21371 strain, ATCC 21369 strain, ATCC 21966 strain, ATCC 21967 strain and ATCC 21969 strain are all currently classified into the genus Methylobacillus and it is further described in International J. Systematic Bacteriology, 36, 502-511, 1986 that ATCC 21276 strain and ATCC 21371 strain are classified into the species *Methylobacillus glycogenes*.

Accordingly, ATCC 21452 strain, ATCC 21276 strain, ATCC 21371 strain, ATCC 21369 strain, ATCC 21966 strain, ATCC 21967 strain and ATCC 21969 strain are hereinafter referred to as Methylobacillus sp. 1001, Methylobacillus sp. 1011, Methylobacillus. sp. 1006, Methylobacillus sp. 1003, Methylobacillus sp. K-015, Methylobacillus sp. K-038 and Methylobacillus sp. K-224, respectively.

In order to enhance the sensitivity of Methylobacillus sp. 1001, Methylobacillus sp. 1011, Methylobacillus sp. 1006 and Methylobacillus sp. 1003 to the chemicals, these wild strains are subjected to a conventional mutational treatment such as NTG treatment. A specific example of the obtained mutant is Methylobacillus sp. iAlll. The procedure for obtaining the iAlll strain is shown below.

Methylobacillus sp. 1011 is cultured in Ml medium having the following composition at 30° C. for 24 hours. The cultured cells are subjected to NTG treatment (500 mg/l, 30° C., 30 minutes) in a conventional manner and then smeared on Ml agar plate medium (Ml medium +1.5% agar) containing 0.1% Casamino acid (manufactured by Difco Laboratories) and 20 mg/l L-tryptophan. After cultivation at 30° C. for 3 to 14 days, colonies formed are picked up and isolated. The thus obtained mutants are inoculated into 3 ml of a seed medium in a test tube, followed by cultivation at 30° C. for 18 hours. Then, 1 ml of the resulting seed culture is inoculated into 50-ml large test tube containing 10 ml of a fermentation medium supplemented with 2% methanol. Cultivation is carried out at 30° C. for 48 hours with further supplementation of 2% methanol 24 hours after the start of the cultivation. Each cultivation described above is carried out with shaking.

The compositions of the culturing media are shown below.

Composition of Ml Medium 0.5% methanol, 0.2% ammonium sulfate, 0.1% potassium dihydrogen phosphate, 0.7% dipotassium hydrogen phosphate, 0.01% sodium chloride, 0.01% thiourea, 0.05% magnesium sulfate, 10 mg/l ferrous sulfate, 8 mg/l manganese sulfate, 1 mg/l thiamine, 0.01 mg/l biotin, pH 7.0.

Composition of Seed Medium [Hereinafter Referred to as Seed Medium (a)]

2% nutrient broth (manufactured by Kyokuto Pharmaceutical Co., Ltd.), 0.5% yeast extract S (manufactured by Daigo Pharmaceutical Co., Ltd.), 1% methanol, pH 7.0.

Composition of Fermentation Medium [Hereinafter Referred to as Fermentation Medium (b)]

0.8% ammonium sulfate, 0.1% potassium dihydrogen phosphate, 0.7% dipotassium hydrogen phosphate, 0.1% sodium chloride, 0.04% magnesium sulfate, 10 mg/l ferrous sulfate, 10 mg/l manganese sulfate, 0.05 mg/l biotin, 0.2 mg/l thiamine, 0.5 mg/l calcium pantothenate, 0.5 mg/l nicotinic acid, 0.3% corn steep liquor, 0.05% Casamino acid, 2% calcium carbonate, pH 7.0.

The pH is adjusted with sodium hydroxide or hydrochloric acid. In preparation of the above media, components other than methanol are dissolved and the solution is sterilized with steam at 120° C. for 15 minutes. Then, methanol which has been passed through a membrane filter (manufactured by Millipore Co., 0.45 μm) for sterilization is added in the amount indicated.

After the completion of cultivation, the cells and calcium carbonate are separated from the culture by centrifugation. The amino acids contained in the supernatant of the culture are analyzed with an amino acid analyzer (manufactured by Nippon Bunko Co., Ltd., high performance liquid chromatography, amino acid analysis system). The strain whose culture supernatant contains amino acids such as gutamic acid, aspartic acid, valine and alanine is selected as an amino acid leaky mutant.

The thus obtained amino acid leaky mutant is examined for sensitivity to chemicals in the following manner. The amino acid leaky mutant is inoculated onto Ml agar plate media containing kanamycin sulfate [Km](manufactured by Meiji Seika Co., Ltd.), ampicillin [Ap](manufactured by Sigma Co., Ltd.), streptomycin sulfate [Sm](manufactured by Nakarai Pharmaceutical Co., Ltd.), AHV (manufactured by Sigma Co., Ltd.) and AEC (manufactured by Sigma Co., Ltd.) at various concentrations. Cultivation is carried out at 30° C. for 2 to 5 days to examine the growth and a strain having an enhanced chemical-sensitivity compared with the parent strain is selected.

A strain having a higher chemical-sensitivity than that of the parent strain, Methylobacillus sp. 1011, is named Methylobacillus sp. iAlll.

The minimum concentration (minimum inhibitory concentration) of each chemical at which the growth of representative strains is inhibited is shown in Table 2. In the case of K-224 strain, the minimum inhibitory concentration was determined using Ml agar medium containing 50 mg/l phenylalanine.

TABLE 2

| Strain | Minimum Inhibitory Concentration of various chemicals (mg/l) | | | | |
|---|---|---|---|---|---|
| | Km | Ap | Sm | AHV | AEC |
| 1011 Strain | 100 | 200 | 200 | >3000 | >3000 |
| iA111 Strain | 20 | 20 | 50 | 1000 | 1000 |
| K-015 Strain | 20 | 50 | 50 | 1000 | 1000 |
| K-038 Strain | 20 | 20 | 50 | 1000 | 500 |
| 1006 Strain | 200 | 200 | 500 | >3000 | >3000 |
| K-224 Strain | 20 | 50 | 50 | 1000 | 1000 |

The method for obtaining the microorganisms used in the present invention is described below.

The microorganisms used in the present invention are mutants obtained by conferring the resistance to at least one member selected from L-Thr, L-Lys and the amino acid analogue on the strains belonging to the genus Methylobacillus described above. Such mutants can be obtained by subjecting the parent strains to a conventional mutation treatment such as a treatment with NTG, and then isolating strains which can grow in or on a medium containing at least one member selected from L-Thr, L-Lys and the amino acid analogue at the concentration at which the parent strains can not grow.

Specific procedures for obtaining the mutants of the present invention are illustrated below.

(1) Method for Obtaining Methylobacillus sp. TA-47

Methylobacillus sp. iAlll is cultured in Ml medium containing 0.1% Casamino acid and 20 mg/l L-tryptophan at 30° C. for 24 hours. The obtained cells are subjected to NTG treatment (500 mg/l, 30° C., 30 minutes), in a conventional manner. The treated cells are smeared on Ml agar plate medium containing 5000 mg/l L-Thr and cultured at 30° C. for 3 to 14 days to obtain cooonies of L-Thr-resistant mutants growable thereon. The colonies are picked up and subjected to L-Thr and L-Lys production test. A mutant having a higher productivity of L-Thr and L-Lys than that of the parent strain is selected and named Methylobacillus sp. TA-47.

(2) Method for Obtaining Methylobacillus sp. DA-19

The same procedure as in (1) above is repeated except that 1000 mg/l L-Lys and 1000 mg/l AHV are added to Ml agar medium in place of 5000 mg/l L-Thr, whereby mutants resistant to L-Lys and AHV are obtained. A mutant having a higher L-Thr productivity than that of the parent strain is selected and named Methylobacillus sp. DA-19.

(3) Method for Obtaining Methylobacillus sp. DA-35

The same procedure as in (1) above is repeated except that 5000 mg/l DHL is added to Ml agar medium in place of 5000 mg/l L-thr, whereby DHL-resistant mutants are obtained A mutant having a higher L-Lys productivity than that of the parent strain is selected and named Methylobacillus sp. DA-35.

DHL was synthesized by the process described in Journal of Biochemistry, 100, 21–25 (1986), with reference to the description in Journal of the American Chemical Society, 83, 2279–2281 (1961), and the product having a purity of more than 97% was used after purification.

TABLE 3

| Strain | Accession Number |
| --- | --- |
| TA-47 Strain | FERM BP-2979 |
| DA-19 Strain | FERM BP-2981 |
| DA-35 Strain | FERM BP-2982 |
| AL-76 Strain | FERM BP-2980 |
| TR-26 Strain | FERM BP-2983 |
| ATR-89 Strain | FERM BP-2984 |

The obtained mutants and their parent strains were cultured on Ml agar medium containing the chemicals(s) described below at 30° C. for 48 hours, and the degree of growth was observed. The results are shown in Table 4.

TABLE 4

| Chemical | Concentration (mg/l) | iA111 | TA-47 | DA-19 | DA-35 | AL-76 | K-224 | TR-26 | ATR-89 |
| --- | --- | --- | --- | --- | --- | --- | --- | --- | --- |
| L-Thr | 0 | + | + | | | | + | + | |
| | 1000 | + | + | | | | − | + | |
| | 5000 | − | + | | | | − | | |
| L-Lys + AHV | 0 + 0 | + | | + | | + | | | |
| | 1000 + 1000 | − | | + | | + | | | |
| | 5000 + 2000 | − | | | | + | | | |
| L-Thr + AEC | 0 + 0 | | | | | | + | | + |
| | 1000 + 1000 | | | | | | − | | + |
| DHL | 0 | + | | | + | | | | |
| | 1000 | + | | | + | | | | |
| | 5000 | − | | | + | | | | |

+: Sufficient growth
−: No growth (4) Method for Obtaining Methylobacillus sp. AL-76

The same procedure as in (1) above is repeated except that 2000 mg/l AHV and 5000 mg/l L-Lys are added to Ml agar medium in place of 5000 mg/l L-Thr, whereby mutants resistant to AHV and L-Lys are obtained. A mutant having a higher L-Lys productivity than that of the parent strain is selected and named Methylobacillus sp. AL-76.

(5) Method for Obtaining Methylobacillus sp. TR-26

The same procedure as in (1) above is repeated except that K-224 strain is used as the parent strain instead of iA111 strain and 1000 mg/l L-Thr is added to Ml agar medium containing 50 mg/l phenylalanine in place of 5000 mg/l L-Thr, whereby L-Thr-resistant mutants are obtained. A mutant having a higher L-Thr productivity than that of the parent strain is selected and named Methylobacillus sp. TR-26.

(6) Method for Obtaining Methylobacillus sp. ATR-89

The same procedure as in (1) above is repeated except that K-224 strain is used as the parent strain instead of iA111 strain and 1000 mg/l L-Thr and 1000 mg/l AEC are added to Ml agar medium containing 50 mg/l phenylalanine in place of 5000 mg/l L-Thr, whereby mutants resistant to L-Thr and AEC are obtained. A mutant having a higher productivity of L-Thr and L-Lys than that of the parent strain is selected and named Methylobacillus sp. ATR-89.

The obtained mutants were deposited with the Fermentation Research Institute, Agency of Industrial Science and Technology, Japan, on Jun. 22, 1990 under the Budapest Treaty. The accession numbers of the respective strains are shown in Table 3.

The microorganisms used in the present invention are cultured by the process generally used for culturing a methanol-assimilating microorganism.

As the medium for the production of amino acids in the present invention, any of synthetic media and natural media may be used so long as it contains carbon sources, nitrogen sources, inorganic materials, and if necessary, organic trace components.

As the carbon source, methanol is mainly used and added to the medium at a concentration of 0.05 to 30%. Organic acids such as pyruvic acid and 2-ketoglutaric acid and natural organic components such as yeast extract, peptone and corn steep liquor, may be added to the medium at a concentration of 0.01 to 4%, if the growth of the microorganism used and/or the production of L-Thr and L-Lys can be promoted by the addition As the nitrogen source, ammonium sulfate, ammonium chloride, ammonium acetate, ammonium nitrate, ammonium phosphate, ammonia gas, aqueous ammonia, urea, etc. may be added to the medium at a concentration of 0.1 to 8%. In addition, small quantities of the trace components such as potassium phosphate, sodium phosphate, magnesium sulfate, ferrous sulfate and manganese sulfate are generally added.

The cultivation is carried out under aerobic conditions, for example, by shaking culture or submerged culture with aeration and agitation at a temperature of 24 to 37° C. and at pH 5 to 9, and is completed generally in 24 to 120 hours.

The amino acids such as L-Thr and L-Lys can be recovered from the culture by removing the precipitates such as cells from the culture and subjecting the resulting supernatant to conventional means such as ion exchange, concentration and salting out. For example, in order to obtain L-Thr, the cell-free culture supernatant is adjusted to pH 2 with hydrochloric acid and then passed through a strongly acidic cation exchange resin (manufactured by Mitsubishi Kasei Co., Ltd.). The adsorbed component is eluted with diluted aqueous ammonia and then ammonia is removed. After concentration, alcohol is added to the concentrate and the crystals formed during storage under cooling are collected to give L-Thr.

In order to obtain L-Lys, the cell-free of the culture supernatant culture is adjusted to pH 7.0 with aqueous solution of sodium hydroxide and then passed through a cation exchange resin (manufactured by Mitsubishi Kasei Co., Ltd.). The adsorbed component is eluted with diluted hydrochloric acid and the fractions corresponding to L-Lys are collected. Alcohol is added to the combined fractions and the crystals formed during storage under cooling are collected to give LLys.

Certain embodiments of the present invention are illustrated in the following examples.

EXAMPLE 1

Production of L-Thr

Methylobacillus sp. TA-47 was inoculated into 3 ml of seed medium (a) in a test tube and cultured with shaking at 30° C. for 18 hours. Then, 1 ml of the culture obtained was added to 10 ml of fermentation medium (b) containing 2% methanol in a 50-ml large test tube and cultured with shaking at 30° C. Twenty four hours after the start of the cultivation, 2% methanol was further added and the cultivation was continued for further 24 hours.

After the completion of cultivation, the cells and calcium carbonate were removed by centrifugation and the concentration of L-Thr contained in the resulting supernatant was determined with an amino acid analyzer (manufactured by Nippon Bunko Co., Ltd., high performance liquid chromatography, amino acid analysis system).

The same procedure as above was repeated using 1011, 1006, iA1ll, K-224, DA-19, TR-26 and ATR-89 strains, respectively, instead of TA-47, and the concentration of L-Thr contained in the supernatant of the culture was determined.

The results are shown in Table 5.

TABLE 5

| Strain | Amount of L-Thr Accumulated (mg/ml) |
| --- | --- |
| 1011 Strain | 0.01 or less |
| iA111 Strain | 0.02 |
| TA-47 strain | 2.0 |
| DA-19 Strain | 1.81 |
| 1006 Strain | 0.01 or less |
| K-224 Strain | 0.04 |
| TR-26 Strain | 0.43 |
| ATR-89 Strain | 1.34 |

EXAMPLE 2

Recovery of L-Thr

TA-47 strain was cultured in the same manner as in Example 1. The resulting culture supernatant (800 ml) was adjusted to pH 2 with hydrochloric acid and then passed through a column packed with strong cation exchange resin, DIAION SKlB (H type)(manufactured by Mitsubishi Kasei Co., Ltd.). After the column was washed with water, the component adsorbed onto the resin was eluted with 2 N aqueous ammonia The fractions containing L-Thr were combined and concentrated under reduced pressure Ethanol was added to the concentrate and the mixture was cooled to 4° C. to form crystals The crystals were collected and dried to give 1.25 g of L-Thr crystals having a purity of 98% or more.

EXAMPLE 3

Production of L-Lys

Methylobacillus sp. strains 1011, iAlll, TA-47, DA-35, AL-76, 1006, K-224 and ATR-89 were respectively cultured in the same manner as in Example 1.

After the completion of cultivation, the concentration of L-Lys contained in the resulting culture supernatant was determined with the amino acid analyzer.

The results are shown in Table 6.

TABLE 6

| Strain | Amount of L-Lys Accumulated (mg/ml) |
| --- | --- |
| 1011 Strain | 0.01 or less |
| iA111 Strain | 0.03 |
| DA-35 Strain | 0.28 |
| TA-47 Strain | 0.33 |
| AL-76 Strain | 0.39 |
| 1006 Strain | 0.01 or less |
| K-224 Strain | 0.02 |
| ATR-89 Strain | 0.15 |

EXAMPLE 4

Production of L-Lys

Two loopfuls of Methylobacillus sp. AL-76 was inoculated into 25 ml of seed medium (a) in a 300-ml Erlenmeyer flask and cultured with shaking at 30° C. for 18 hours. The whole seed culture was transferred to a 2-l Erlenmeyer flask containing 225 ml of seed medium (a). Cultivation was carried out with shaking at 30° C. for further 18 hours.

The whole of the resulting seed culture (250 ml) was inoculated into 2.25 l of fermentation medium (b) in a 5-l fermentor (manufactured by Mitsuwa Biosystem Co., Ltd.). Cultivation was carried out at 30° C. with agitation (600 rpm) and aeration (2.5 l/min). During the cultivation, pH of the medium was automatically adjusted to 6.8 with 6 N $NH_4OH$ solution. Methanol was added at a concentration of 0.5% at the start of the cultivation and then continuously added in such an amount that the concentration of 0.5% is maintained, using a perista pump (manufactured by Ato Co., Ltd.).

By cultivation for 72 hours, 3.02 g/l L-Lys was accumulated in the medium.

EXAMPLE 5

Recovery of L-Lys

AL-76 Strain was cultured in the same manner as in Example 4. The culture supernatant (1200 ml) obtained by centrifugation was adjusted to pH 7.0 with sodium hydroxide and then passed through a column packed with strong cation exchange resin, DIAION SKlB ($NH_3$ type)(manufactured by Mitsubishi Kasei Co., Ltd.). After the column was washed with water, the component adsorbed onto the resin was eluted with 1 N hydrochloric acid. The fractions containing L-Lys were combined and concentrated under reduced pressure. Ethanol was added to the concentrate and the mixture was cooled to 4° C. to form crystals The crystals were collected and dried to give 1.88 g of crystals of L-Lys hydrochloride having a purity of 96% or more.

What is claimed is:

1. A process for producing an amino acid selected from the group consisting of L-threonine and L-lysine, comprising:
   providing a mutant belonging to the genus Methylobacillus having an enhanced sensitivity to at least one of an antibiotic and an amino acid analogue wherein said mutant is obtained by subjecting a microorganism belonging to the genus methylobacillus to a prior mutation treatment,
   subjecting said mutant to a subsequent mutation treatment,
   selecting and isolating mutants having ability to produce the amino acid selected from the group consisting of L-threonine and L-lysine and having resistance to at least one of L-threonine, L-lysine and an amino acid analogue,
   cultivating said mutant in a medium including methanol as a carbon source,
   allowing the amino acid selected from the group consisting of L-threonine and L-lysine to accumulate, and
   recovering the amino acid selected from the group consisting of L-threonine and L-lysine therefrom said microorganism subjected to the prior mutation treatment being selected from the group consisting of Methylobacillus sp. 1001 (ATCC 21452), Methylobacillus sp. 1003 (ATCC 21369), Methylobacillus sp. 1006 (ATCC 21371) and Methylobacillus sp. 1011 (ATCC 21276).

2. A process according to claim 1, wherein said antibiotic is selected from the group consisting of kanamycin, ampicillin and streptomycin.

3. A process according to claim 1 wherein said amino acid analogue is selected from the group consisting of α-amino-β-hydroxyvaleric acid, S-2-aminoethyl-L-cysteine and DL-4,5-transdehydrolysine.

4. A process according to claim 1, wherein the mutation treatment are selected from the group consisting of UV irradiation and chemical treatment.

5. A process according to claim 4 wherein the chemical treatment is chemical treatment with N-methyl-N'-nitronitrosoguanidine.

6. A process for producing an amino acid selected from the group consisting of L-threonine and L-lysine comprising:
   cultivating a microorganism selected from the group consisting of Methylobacillus sp. TA-47 (FERM BP-2979), Methylobacillus sp. DA-19 (FERM BP-2981), Methylobacillus sp. AL 76 (FERM BP-2980), Methylobacillus sp. TR-26 (FERM BP-2983) and Methylobacillus sp. ATR-89 (FERM BP-2984) in a medium including methanol as carbon source,
   allowing the amino acid selected from the group consisting of L-threonine and L-lysine to accumulate, and
   recovering the amino acid selected from the group consisting of L-threonine and L-lysine therefrom.

* * * * *